(12) United States Patent
Freedman et al.

(10) Patent No.: US 7,647,240 B2
(45) Date of Patent: Jan. 12, 2010

(54) COMPUTER-IMPLEMENTED SYSTEM AND METHOD FOR MATCHING CLINICAL RESEARCH MONITORS WITH CLINICAL TRIAL SPONSORS

(75) Inventors: Scott D. Freedman, Lafayette Hill, PA (US); Rod M. Saponjic, San Diego, CA (US)

(73) Assignee: Pharma eMarket LLC, Newark, DE (US)

( * ) Notice: Subject to any disclaimer, the term of this patent is extended or adjusted under 35 U.S.C. 154(b) by 1306 days.

(21) Appl. No.: 10/298,316

(22) Filed: Nov. 18, 2002

(65) Prior Publication Data

US 2003/0097291 A1    May 22, 2003

Related U.S. Application Data

(60) Provisional application No. 60/331,833, filed on Nov. 20, 2001.

(51) Int. Cl.
G06F 9/46 (2006.01)
G06F 15/02 (2006.01)
G06Q 10/00 (2006.01)
G06Q 50/00 (2006.01)

(52) U.S. Cl. .............................. 705/9; 705/2
(58) Field of Classification Search .......... 705/8, 705/32, 9, 2
See application file for complete search history.

(56) References Cited

U.S. PATENT DOCUMENTS

| | | | | |
|---|---|---|---|---|
| 5,189,606 | A * | 2/1993 | Burns et al. | 705/10 |
| 5,862,223 | A * | 1/1999 | Walker et al. | 705/50 |
| 6,747,679 | B1 * | 6/2004 | Finch et al. | 715/777 |
| 6,950,801 | B2 * | 9/2005 | Brookes et al. | 705/8 |
| 7,089,203 | B1 * | 8/2006 | Crookshanks | 705/37 |
| 7,167,855 | B1 * | 1/2007 | Koenig | 707/3 |
| 2001/0051882 | A1 * | 12/2001 | Murphy et al. | 705/3 |
| 2002/0002474 | A1 * | 1/2002 | Michelson et al. | 705/3 |

(Continued)

OTHER PUBLICATIONS www.monitorforhire.com.*

(Continued)

*Primary Examiner*—Beth V Boswell
*Assistant Examiner*—Folashade Anderson
(74) *Attorney, Agent, or Firm*—RatnerPrestia (57) ABSTRACT

A computer-implemented system and method that prescreens the qualifications of clinical monitors, and quickly and efficiently matches qualified monitors with corresponding qualified clinical sponsors for work on a project. The system and method provide a secure platform for storage and searching of monitor profiles that may be continuously updated by the monitors. The system and method also checks the qualifications provided by monitors in their profiles to ensure that only qualified monitors are capable of being searched by the sponsors. The system and method also provides a secure platform for sponsors to post their clinical projects, and enables the sponsors to select the monitors they wish to view the project details. The system and method then provides the details of the project to the selected monitors, and the ones who are interested may be subsequently interviewed and selected by the sponsors. The system and method also provides a mechanism so that the sponsors and monitors may enter a contract regarding the project. The system and method dramatically reduces the time searching for qualified monitors needed to conduct studies, reduces costs for sponsors, and enables studies to be organized and started more efficiently.

28 Claims, 7 Drawing Sheets

U.S. PATENT DOCUMENTS

2005/0216323 A1* 9/2005 Weild .......................... 705/7

OTHER PUBLICATIONS

"CB Technologies and MonitorForHire.Com Partner to Certify Independent Clinical Monitors on MetaTrial EDC." PR Newswire. Jul. 5, 2001. p. 1.*

"Pharmaceutical Industry Embraces Clinmark Dotcom; Success Stories Abound For The Industry's Largest Internet-Based Investigator Database" Business Wire. Jul. 6, 1998 p. 1.*

"Terms of Service." Guru. 2001. May 17, 2008 <http://www.guru.com>.*

* cited by examiner

COMPUTER-IMPLEMENTED SYSTEM AND METHOD FOR MATCHING CLINICAL RESEARCH MONITORS WITH CLINICAL TRIAL SPONSORS

The present application claims priority of U.S. Provisional Patent Application Ser. No. 60/331,833, filed Nov. 20, 2001, the disclosure of which being incorporated by reference herein in its entirety.

BACKGROUND OF THE INVENTION

A. Field of the Invention

The present invention relates generally to the clinical research field, and, more particularly to a computer-implemented system and method for matching clinical research monitors with clinical trial sponsors.

B. Description of the Related Art

Clinical research monitors (hereinafter referred to as "clinical monitors," "CRMs," or "monitors") are responsible for auditing clinical trials that are conducted to evaluate new drug candidates. The job of the monitor is to ensure that clinical trial sponsors (e.g., clinical research organizations ("CROs"), pharmaceutical companies, biotechnology companies, medical device companies, etc., hereinafter referred to as "clinical sponsors" or "sponsors"), primarily doctors and medical researchers, adhere to the study protocols approved by the Food and Drug Administration ("FDA"). Monitors play a key role in the drug development process, where a single lost day can translate into $1 million in missed product revenues.

Once a sponsor is ready to begin a clinical study, they will typically look to hire independent contractors to serve as monitors. Finding qualified monitors typically is a laborious and time-consuming task, which does not fit well in an industry where research and development productivity thrives on a sponsor's ability to get trials up and running quickly. In the typical process of staffing a project with monitors, the sponsor contacts a staffing agency that represents a select group of monitors, and provides a list of qualifications needed for monitors for the project. The staffing agency will then search through its list of monitors and locate qualified monitors for the project. Often, however, the staffing company will contact the list of qualified monitors, and find that some or all of them are unavailable for project. Using this traditional method, generally requires four to six weeks to fully staff a project, depending upon the size of the project and the number of monitors required.

In some instances, the staffing agency fails to properly prescreen the credentials of the monitors it is representing and offering to sponsors. Failure to prescreen monitors may result in unqualified monitor(s) being selected for a project by a sponsor. The inadequacies of such unqualified monitors may not be readily evident to the sponsor, which may result in improper clinical trials being performed. Once the inadequacies of the unqualified monitor are discovered, the sponsor will need to replace the unqualified monitor and may lose valuable time while trying to complete the clinical trials.

The traditional method of matching monitors with sponsors costs sponsors significant time and money. This is unacceptable in the highly-competitive industry of drug development where a single lost day of clinical research may cost a sponsor significant sums of revenue.

Thus there is a need in the art to provide a secure mechanism for quickly and efficiently matching prescreened, qualified monitors with corresponding sponsors

SUMMARY OF THE INVENTION

The present invention satisfies the need of the related art by providing a computer-implemented system and method for prescreening clinical research monitors, and quickly and efficiently matching qualified clinical research monitors with corresponding clinical sponsors.

Additional advantages of the invention will be set forth in part in the description which follows, and in part will be learned from the description, or may be learned by practice of the invention. The advantages of the invention will be realized and attained by means of the elements and combinations particularly pointed out in the appended claims.

In accordance with the purpose of the invention, as embodied and broadly described herein, the invention comprises a computer-implemented method for matching clinical research monitors with clinical sponsors, including: (i) creating a monitor profile for each clinical research monitor by inputting information selected from one or more of the following: login information, personal information, foreign language skills, contact information, company information, education information, certification information, work history, professional affiliations, therapeutic specialties, references, calendar of availability; (ii) prescreening the monitor profiles to ensure they meet predetermined qualifications; (iii) securely storing the monitor profiles; (iv) inputting project information from the clinical sponsors selected from one or more of the following: company name, project name, start and end dates, therapeutic specialty, indication, phase, percent of time commitment, number of subjects per site, sites per monitor, estimated CRF pages per patient, whether pre-study visits are required, whether initiation visits are required, estimated days on site, and study site locations; (v) securely storing the project information; (vi) enabling the clinical sponsors to search the blinded monitor profiles for qualified clinical monitors based upon predetermined search criteria; (vii) enabling the clinical sponsors to select the clinical monitors to view the project; (viii) automatically generating email invitations to the selected clinical monitors, informing them that they have been selected to interview for a project, and requesting that they review the project information; and (ix) upon acceptance of the invitation by the clinical monitors, subsequently unblinding the contact information for each monitor to the clinical sponsors.

Further in accordance with the purpose of the invention, as embodied and broadly described herein, the invention comprises a system for matching clinical research monitors with clinical sponsors, the system including: a memory configured to store instructions; and a processor configured to execute instructions for: (i) creating a monitor profile for each clinical research monitor by inputting information selected from one or more of the following: login information, personal information, foreign language skills, contact information, company information, education information, certification information, work history, professional affiliations, therapeutic specialties, references, and calendar of availability; (ii) prescreening the monitor profiles to ensure they meet predetermined qualifications; (iii) securely storing the monitor profiles; (iv) inputting project information from the clinical sponsors selected from one or more of the following: company name, project name, start and end dates, therapeutic specialty, indication, phase, percent of time commitment, number of subjects per site, sites per monitor, estimated CRF pages per patient, whether pre-study visits are required, whether initiation visits are required, estimated days on site, and study site locations; (v) securely storing the project information; (vi) enabling the clinical sponsors to search the blinded monitor profiles for qualified clinical monitors based upon predetermined search criteria; (vii) enabling the clinical sponsors to select the clinical monitors to view the project; (viii) automatically generating email invitations to the selected clinical monitors, informing them that they have been selected to interview for a project, and requesting that they review the project information; and (ix) upon acceptance of the invitation by the clinical monitors, subsequently unblinding the contact information for each monitor to the clinical sponsors.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIGS. 4(*a*)-4(*d*) is a flow chart of processing performed by a client, server, or client/server entity shown in FIG. 3.

DETAILED DESCRIPTION OF EMBODIMENTS OF THE INVENTION

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

The globally-linked network of computers known as the Internet presents many opportunities today. The world-wide web (WWW), which is one of the facilities provided on top of the Internet, comprises many pages or files of information, distributed across many different server computer systems. Information stored on such pages can be presented to the user's computer system ("client computer system") using a combination of text, graphics, audio data and video data. Each page is identified by a Universal Resource Locator (URL). The URL denotes both the server machine, and the particular file or page on that machine. There may be many pages or URLs resident on a single server.

In order to use the WWW, a client computer system runs a piece of software known as a graphical web browser, such as the Navigator® program available from Netscape® Communications Corporation. The client computer system interacts with the browser to select a particular URL, which in turn causes the browser to send a request for that URL or page to the server identified in the URL. Typically the server responds to the request by retrieving the requested page, and transmitting the data for that page back to the requesting client computer system (the client/server interaction is performed in accordance with the hypertext transport protocol ("HTTP")). This page is then displayed to the user on the client screen. The client may also cause the server to launch an application, for example to search for WWW pages relating to particular topics. Most WWW pages are formatted in accordance with a computer program written in a language known as HTML (hypertext markup language). This program contains the data to be displayed via the client's graphical browser as well as formatting commands which tell the browser how to display the data. Thus a typical web page includes text together with embedded formatting commands, referred to as tags, which can be used to control the font size, the font style (for example, whether italic or bold), how to layout the text, and so on. A web browser "parses" the HTML script in order to display the text in accordance with the specified format. HTML tags are also used to indicate how graphics, audio and video are manifested to the user via the client's browser.

The Internet is a channel well suited for sponsors looking to quickly locate and contract with independent monitors. The present invention makes use of the opportunities afforded by the Internet to provide a computer-implemented system and method for prescreening monitors, and quickly and efficiently matching qualified monitors with corresponding sponsors. The present invention provides an efficient, confidential and secure way to identify qualified and available independent clinical monitors who perform reviews of clinical investigative sites, data collection, and adhere to "Good Clinical Practice" as mandated by the FDA. Thus, the present invention dramatically reduces the time searching for qualified monitors needed to conduct studies, reduces costs for sponsors, and enables studies to be organized and started more efficiently.

Figure 1:
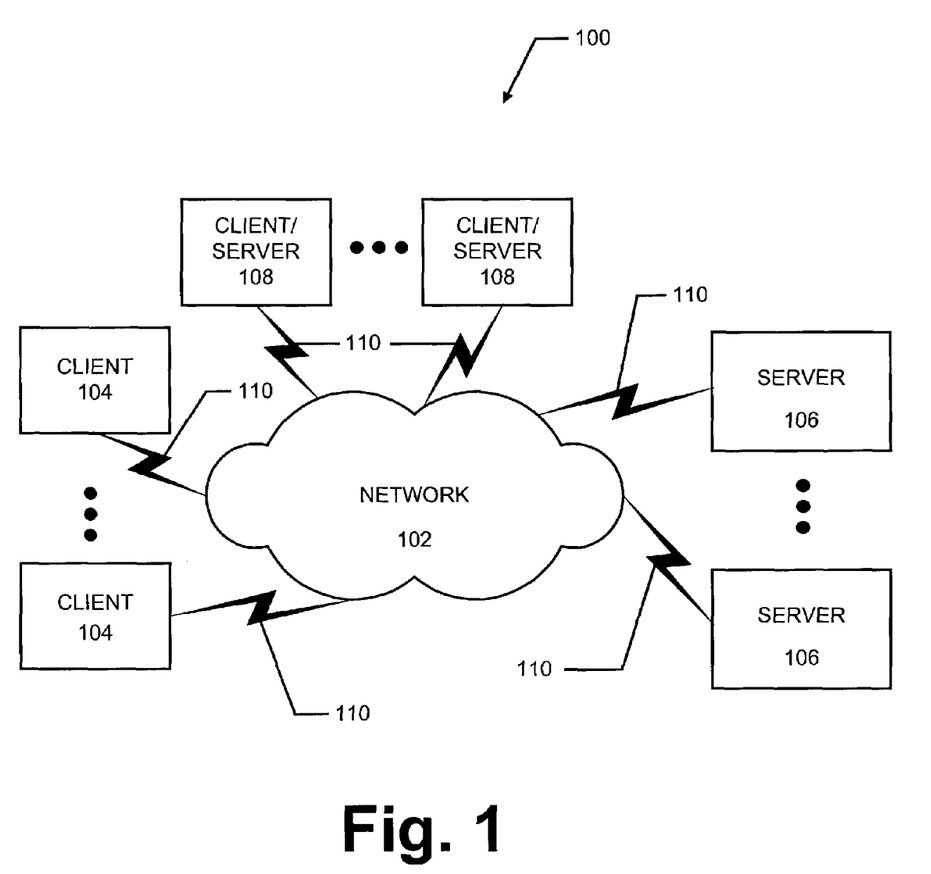
FIG. 1 is a schematic diagram showing a system of an embodiment of the present invention.

In accordance with the invention and as shown in FIG. 1, the system 100 of the present invention includes a network 102 that interconnects client entities 104, server entities 106 and client/server entities 108 via communication links 110.

Network 102 may comprise an Internet, intranet, extranet, local area network (LAN), wide area network (WAN), metropolitan area network (MAN), telephone network such as the public switched telephone network (PSTN), or a similar network.

The Internet is a collection of interconnected (public and/or private) networks that are linked together by a set of standard protocols (such as TCP/IP and HTTP) to form a global, distributed network. While this term is intended to refer to what is now commonly known as the Internet, it is also intended to encompass variations which may be made in the future, including changes and additions to existing protocols.

An intranet is a private network that is contained within an enterprise. It may consist of many interlinked local area networks and also use leased lines in the wide area network. Typically, an intranet includes connections through one or more gateway computers to the outside Internet. The main purpose of an intranet is to share company information and computing resources among employees. An intranet can also be used to facilitate working in groups and for teleconferences. An intranet uses TCP/IP, HTTP, and other Internet protocols and in general looks like a private version of the Internet. With tunneling, companies can send private messages through the public network, using the public network with special encryption/decryption and other security safeguards to connect one part of their intranet to another. Typically, larger enterprises allow users within their intranet to access the public Internet through firewall servers that have the ability to screen messages in both directions so that company security is maintained. When part of an intranet is made accessible to customers, partners, suppliers, or others outside the company, that part becomes part of an extranet.

An extranet is a private network that uses the Internet protocols and the public telecommunication system to securely share part of a business's information or operations with suppliers, vendors, partners, customers, or other businesses. An extranet can be viewed as part of a company's intranet that is extended to users outside the company.

A LAN refers to a network where computing resources such as PCs, printers, minicomputers, and mainframes are linked by a common transmission medium such as coaxial cable. A LAN usually refers to a network in a single building or campus. A WAN is a public or private computer network serving a wide geographic area. A MAN is a data communication network covering the geographic area of a city, a MAN is generally larger than a LAN but smaller than a WAN.

PSTN refers to the world's collection of interconnected voice-oriented public telephone networks, both commercial and government-owned. It is the aggregation of circuit-switching telephone networks that has evolved from the days of Alexander Graham Bell. Today, PSTN is almost entirely digital in technology except for the final link from the central (local) telephone office to the user. In relation to the Internet, the PSTN actually furnishes much of the Internet's long-distance infrastructure.

An entity may include software, such as programs, threads, processes, information, databases, or objects; hardware, such as a computer, a laptop, a personal digital assistant (PDA), a wired or wireless telephone, or a similar wireless device; or a combination of both software and hardware. A client entity 104 is an entity that sends a request to a server entity and waits for a response. A server entity 106 is an entity that responds to the request from the client entity. A client/server entity 108 is an entity where the client and server entities reside in the same piece of hardware or software.

Connections 110 may be wired, wireless, optical or a similar connection mechanisms. "Wireless" refers to a communications, monitoring, or control system in which electromagnetic or acoustic waves carry a signal through atmospheric space rather than along a wire. In most wireless systems, radio-frequency (RF) or infrared (IR) waves are used. Some monitoring devices, such as intrusion alarms, employ acoustic waves at frequencies above the range of human hearing.

Figure 2:
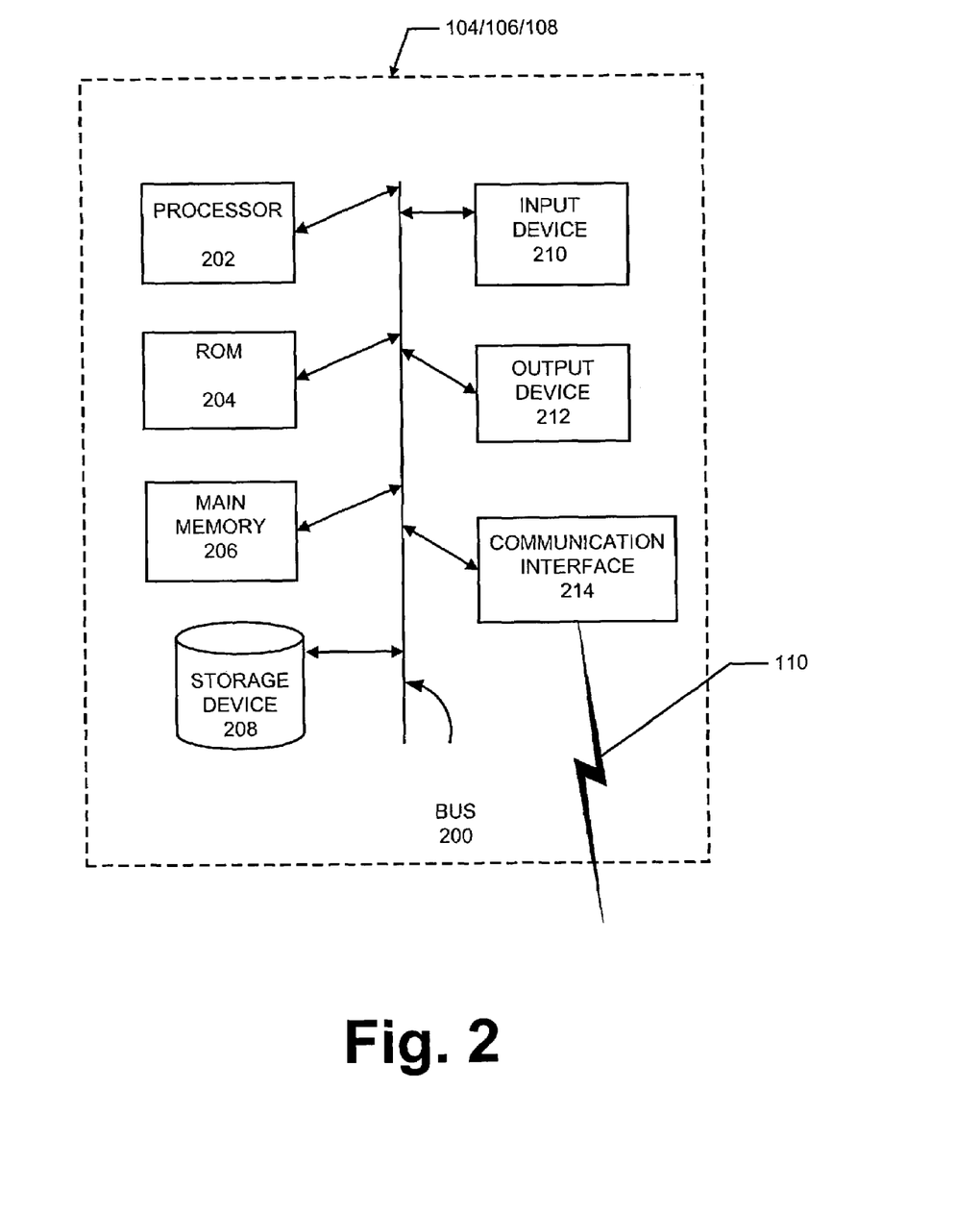
FIG. 2 is a schematic diagram showing a client, server, or client/server of the system of FIG. 1.

As shown in FIG. 2, an entity, whether it be a client entity 104, a server entity 106, or a client/server entity 108, includes a bus 200 interconnecting a processor 202, a read-only memory (ROM) 204, a main memory 206, a storage device 208, an input device 210, an output device 212, and a communication interface 214. Bus 200 is a network topology or circuit arrangement in which all devices are attached to a line directly and all signals pass through each of the devices. Each device has a unique identity and can recognize those signals intended for it. Processor 202 includes the logic circuitry that responds to and processes the basic instructions that drive entity 104, 106, 108. ROM 204 includes a static memory that stores instructions and date used by processor 202.

Computer storage is the holding of data in an electromagnetic form for access by a computer processor. Main memory 206, which may be a RAM or another type of dynamic memory, makes up the primary storage of entity 104, 106, 108. Secondary storage of entity 104, 106, 108 may comprise storage device 208, such as hard disks, tapes, diskettes, Zip drives, RAID systems, holographic storage, optical storage, CD-ROMs, magnetic tapes, and other external devices and their corresponding drives.

Input device 210 may include a keyboard, mouse, pointing device, sound device (e.g. a microphone, etc.), biometric device, or any other device providing input to entity 104, 106, 108. Output device 212 may comprise a display, a printer, a sound device (e.g. a speaker, etc.), or other device providing output to entity 104, 106, 108. Communication interface 214 may include network connections, modems, or other devices used for communications with other computer systems or devices.

As will be described below, an entity 104, 106, 108 consistent with the present invention may perform the method of prescreening and matching qualified monitors with corresponding sponsors. Entity 104, 106, 108 performs this task in response to processor 202 executing sequences of instructions contained in a computer-readable medium, such as main memory 206. A computer-readable medium may include one or more memory devices and/or carrier waves.

Execution of the sequences of instructions contained in main memory 206 causes processor 202 to perform processes that will be described later. Alternatively, hardwired circuitry may be used in place of or in combination with software instructions to implement processes consistent with the present invention. Thus, the present invention is not limited to any specific combination of hardware circuitry and software.

Figure 3:
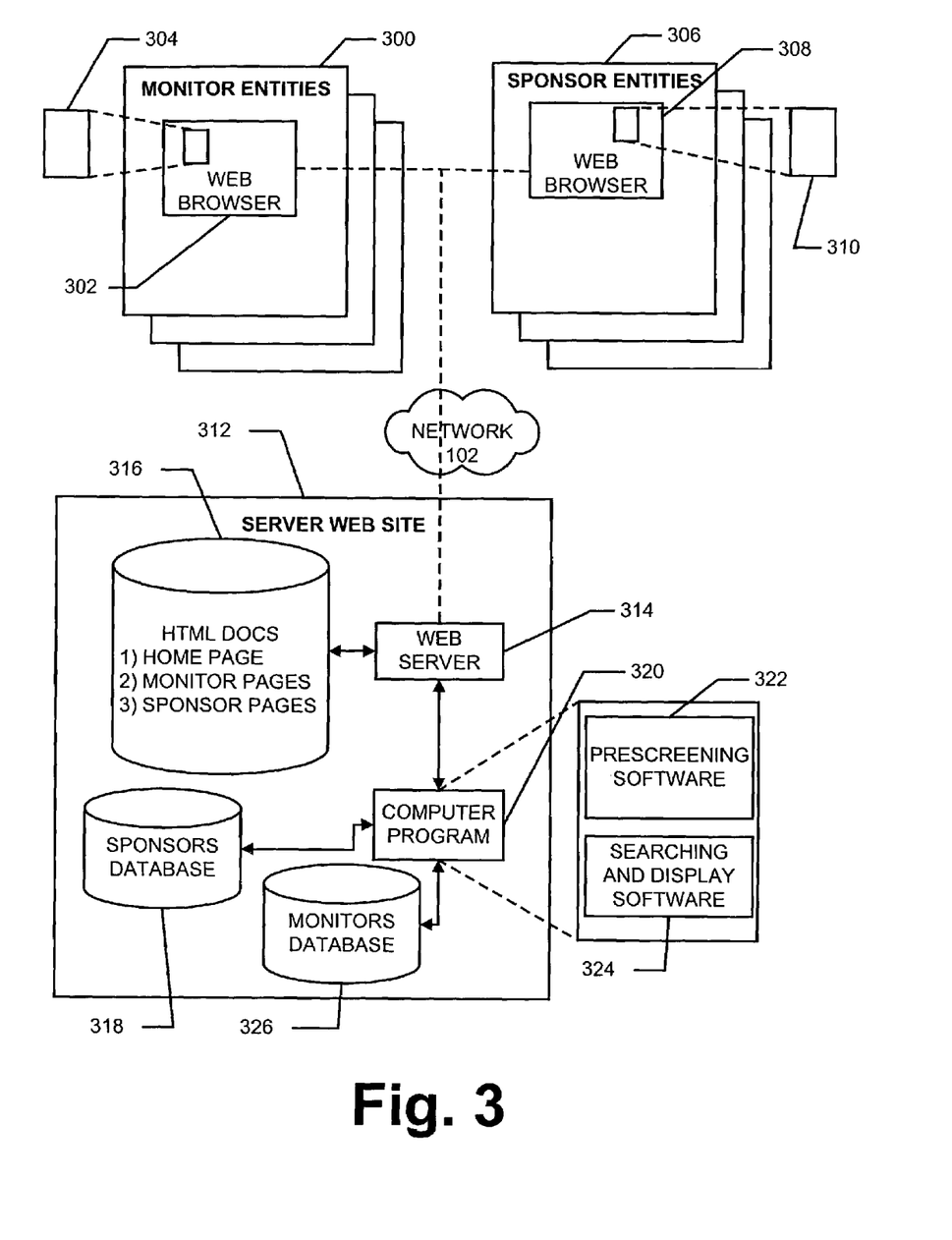
FIG. 3 is a schematic diagram showing the primary components of the system shown in FIG. 1.

As shown in FIG. 3, network 102 interconnects monitor entities 300 and sponsor entities 306 with a server web site entity 312. As used herein, the term "monitor entity" shall mean a client entity, client/server entity, or server entity that is being utilized by a clinical research monitor. Likewise, as used herein, the term "sponsor entity" shall mean a client entity, client/server entity, or server entity that is being utilized by a clinical sponsor.

Monitor entities 300 have web browsers 302 that allow the monitor entities 300 to interactively browse web sites and web documents 304 contained therein. Sponsor entities 306 similarly have web browsers 308 that allow the sponsor entities 306 to interactively browse web sites and web documents 310 contained therein.

Server web site entity 312 contains a web server 314 that interconnects with a database 316 containing HTML documents such as, for example, a Home page, Monitor pages, and Sponsor pages, as more fully described below. Web server 314 further connects to a search engine 320 capable of running a plurality of software processes such as Prescreening software 322, and Searching and Display software 324. Search engine 320 connects to a database 318 for storage of information provided by sponsor entities 306, and further connects to a database 326 for storage of information provided by monitor entities 300.

When a user, whether it be a monitor entity 300 or a sponsor entity 306, connects with server web site entity 312, a Home page is displayed which allows the user to login as a monitor or a sponsor, and, if the user is not registered, permits free registration of the user as a monitor or a sponsor. In order to register, a user must submit information to web server entity 312 by providing information in fields, in a conventional manner, on web server entity 312, or by filling out a form and mailing the form to the operator of web site entity 312. For example, a monitor may input information such as login information (user identification and password), foreign language skills, personal information (name), contact information (address, telephone number, facsimile number, and email address), company information (company name and address), education information, certification information (e.g., certified by a medical or industry organization), work history, professional affiliations, therapeutic specialties, and references. All of this information is used to create a monitor profile, and is stored in monitors database 326 of server web site entity 312. To be approved for listing on web site server entity 312, monitors must go through a screening process, using a prescreening software 322 but preferably using a human resources firm, that checks references and confirms the information inputted by the monitor.

Likewise, a sponsor may be required to submit information such as login information (user identification and password), company name, type of company (e.g., pharmaceutical company, CRO, biotechnology company, etc.) business address, telephone number, email address, etc. All of this information is used to create a sponsor profile, and is in stored sponsors database 318 of server web site entity 312. Manual prescreening of sponsors is also performed prior to allowing sponsors to access server web site entity 312 in a manner similar to way monitors are prescreened.

Once approved, a monitor may access web site server entity 312 by inputting his/her user identification and password at the Home page of web site server entity 312. Web site server entity 312 of the present invention offers independent clinical monitors a single resource with powerful tools to manage their career. By publishing their exact availability to potential sponsors, monitors can work on multiple projects, as well as better balance their career and home lives. This helps to reduce costs for sponsors, and those savings are passed on to monitors in the form of better hourly rates than available under conventional staffing schemes.

Web site server entity 312 of the present invention permits monitors to keep a dynamic resume stored in monitors database 326 that tells potential sponsors the experience a monitor has to offer, e.g., therapeutic expertise, education, references, etc. A monitor can update their profile at any time as they gain new experience and specialties, in a manner similar to way the profile was originally created. Furthermore, a sponsor cannot access certain personal information of a monitor profile (name or contact information) unless the monitor wants to participate in a particular project.

An availability section is also a provided for monitors on web site server entity 312, which offers monitors the ultimate in flexibility in managing their work schedule. By keeping this section up to date, a monitor may inform potential sponsors of their exact availability each month. Each registered monitor also receives his/her own private email account through web site server entity 312. Sponsors may use this email account to communicate with monitors during the course of a project.

A projects section is also a provided for monitors on web site server entity 312, where monitors will find information on projects for which they have been invited and assigned by a sponsor. The selected monitor is free to choose those projects they are interested in working on. A discussion forums section is also a provided on web site server entity 312 that permits monitors and sponsors to share information and collaborate on projects, reducing the duplication of effort among team members.

Monitors use online timesheets, provided on web site server entity 312, to track and record their hours worked, and are automatically paid upon receipt of payment from the sponsor. Web site server entity 312 generates invoices for the monitors, based upon their timesheets, and an outside service will handle the payroll transactions and directly deposit the amounts due to the monitors electronically into their bank accounts.

A registered and approved sponsor may access web site server entity 312 by inputting their user identification and password at the Home page of web site server entity 312. Web site server entity 312 of the present invention offers sponsors a better way to quickly resource projects with the right monitors. Sponsors can calculate resourcing needs, locate independent clinical monitors with the appropriate skills (singly and in teams), and track project billing, all through the secure web site server entity 312. Web site server entity 312 offers sponsors all the services of a conventional agency, but uses Internet technology to offer more control over the review process, increases overall efficiency, and reduces costs.

A registered and approved sponsor will have access to their profile, including the basic information about the sponsor and its company. A sponsor can update their profile at any time, in a manner similar to way the profile was originally created. Web site server entity 312 also provides sponsors with access to a "Monitor Calculator," which helps sponsors estimate their resourcing needs for a project. With the Monitor Calculator, a sponsor may enter the numbers of sites and subjects, the number and types of visits necessary, and the number of CRF (Case Report Form, which is a paper document where the Doctor conducting the clinical study inputs data on patients) pages. The Monitor Calculator calculates and suggests the appropriate number of monitors needed for a project. All of the information entered by the sponsor into the Monitor Calculator is maintained in confidence by web site server entity 312.

Sponsors record information about their projects in a Project Management section provided by web site server entity 312, which is also maintained in confidence. Only monitors that have been selected by the sponsor can view the details of their projects on a secure page. Project information that may be inputted by sponsors, and stored in sponsors database 318, include, for example, company name, project name, start and end dates, therapeutic specialty, indication, phase, percent of time commitment, number of subjects per site, sites per monitor, estimated CRF pages per patient, whether pre-study visits are required, whether initiation visits are required, estimated days on site, study site locations, etc. Additionally, there is a public forum section provided on web site server entity 312 for sponsors and monitors to collaborate on projects, exchange information, and review timesheets.

After defining their project in the Project Management section of the web site server entity 312, sponsors may select and contract with monitors, as shown in FIGS. 4(*a*)-4(*d*) and described below. The method of matching (selecting and contracting) monitors and sponsors in accordance with the present invention is shown generally in FIGS. 4(*a*)-4(*d*) as reference number 400. The method of matching monitors and sponsors is performed predominantly by web site server entity 312, except where noted below. The method generally consists of three parts: (1) sponsor search and selection of monitors (steps 402-408, as shown in FIG. 4(*a*)); (2) sponsor and monitor review details of the project (steps 410-418, as shown in FIG. 4(*b*)); and (3) sponsor contracts with the monitor and commences the project (steps 420-430, as shown in FIGS. 4(*c*) and 4(*d*)).

Figure 4A:
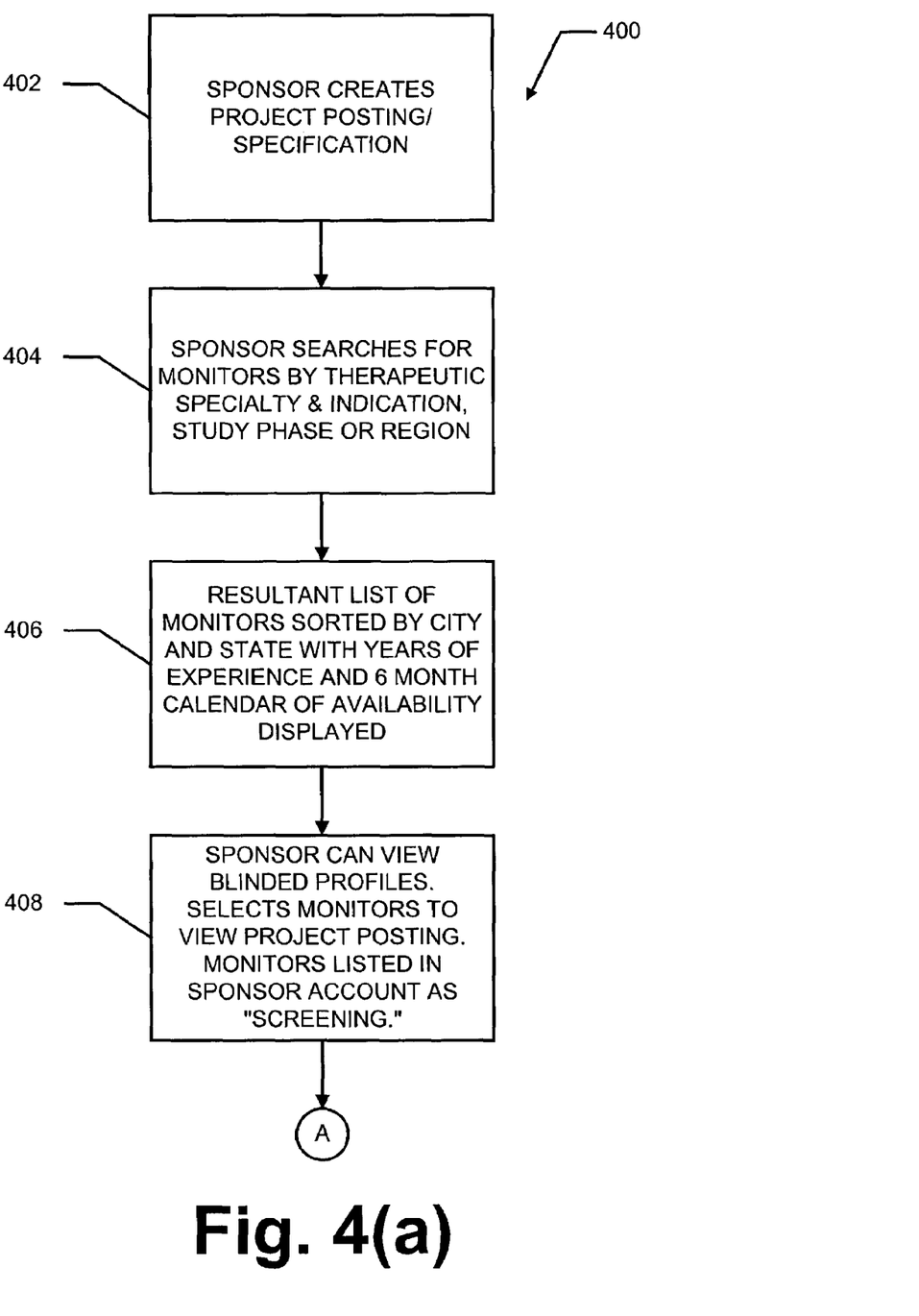

In a first step 402, the sponsor creates a project, as described above, and confidentially inputs the project metrics on web site server entity 312. Then, in step 404, the sponsor searches for monitors based upon various parameters, including but not limited to region, therapeutic specialty, indication experience, and study phase (there are typically four phases to drug development, each phase is distinct, and the type of trial and expertise required for each phase is different). At step 406, the method of the present invention sorts the resultant list of monitors by city and state, and displays the monitors' years of experience and six-month calendar of availability. Sponsors may only view "blinded" monitor profiles at this time. That is, the monitors' name and contact information are not displayed to the sponsors at this time. Once the monitor(s) agrees to be a part of a project, the name and contact information are supplied to the sponsor.

Figure 4B:
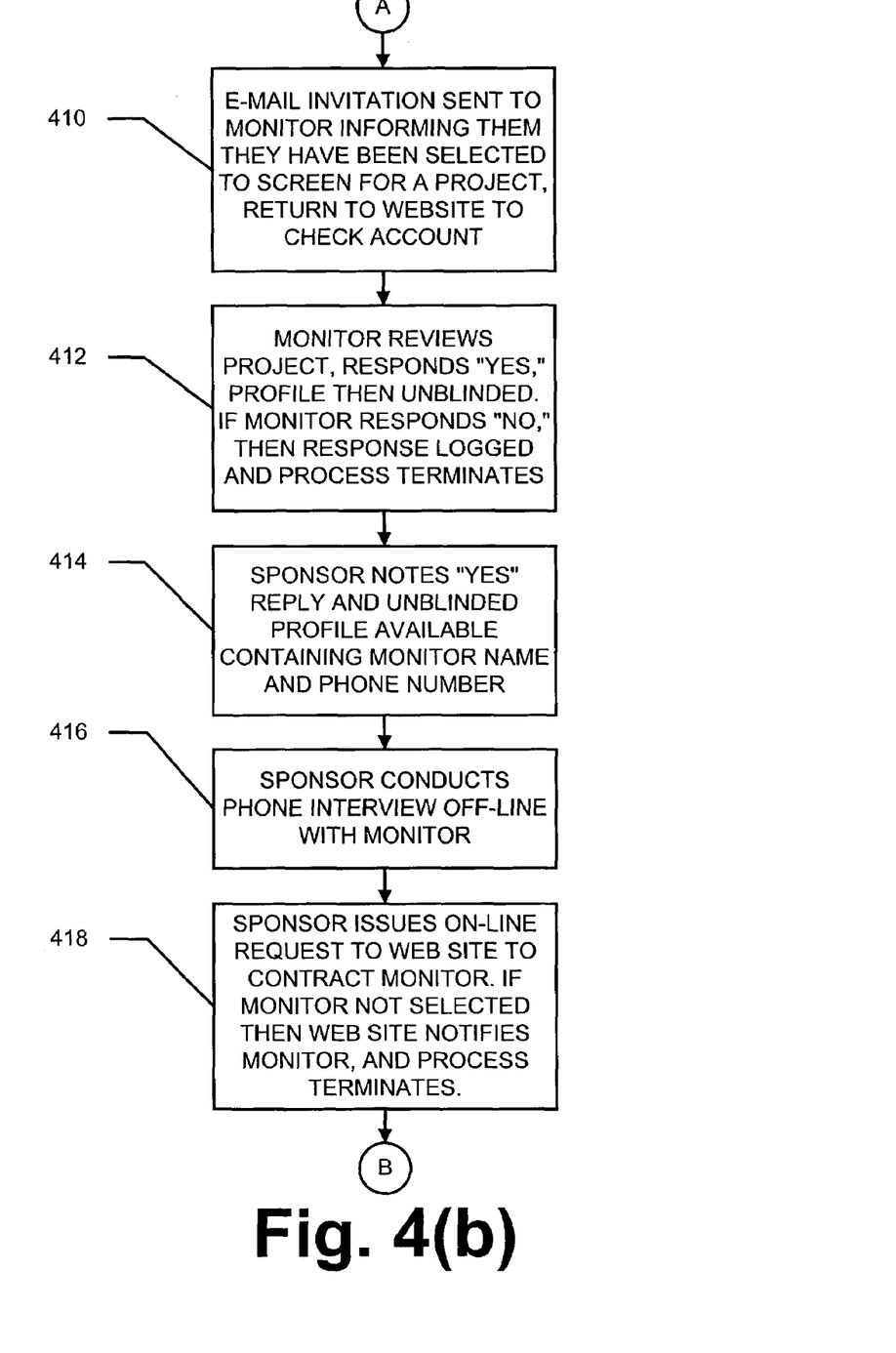

At step 408, the sponsor selects the monitors to view the project information. By querying the database and choosing which monitors they would like to review the project, the sponsor retains all the control of who actually sees the information about the project. Selected monitors are then listed in the sponsor's account as "screening," meaning they are candidates for the project but have not accepted or been approved for the project. Web site server entity 312, at step 410, then automatically generates email invitations to the selected monitors, informing them that they have been selected to screen for a project, and requesting that they log into web site server entity 312 to review the project. At step 412, the selected monitors review the project and either accepts (by, for example, responding "Accept") or rejects (by, for example, responding "Decline") the offer. If the selected monitor accepts the offer, then his/her profile becomes "unblinded" (i.e., name and contact information of monitor displayed) to the sponsor. If the selected monitor rejects the offer, his/her profile remains "blinded", drops off the sponsors screening list, and the method ceases for that monitor.

At step 414, the sponsor receives an "Accept" reply from the monitor(s) that have accepted the project, and may then review the monitor's "unblinded" profile containing the monitor name and contact information (e.g., telephone number). The sponsor then conducts off-line telephone or personal interviews with the selected monitors, at step 416, to determine if the monitors should be selected for the project. At step 418, the sponsor may either request a contract with a monitor, by sending a "request to contract" message to web site server entity 312, or not select a monitor by deleting the monitor. If a monitor is not selected for the project, web site server entity 312 notifies the unselected monitor (e.g., via email or telephone), and the method terminates for the unselected monitor.

Figure 4C:
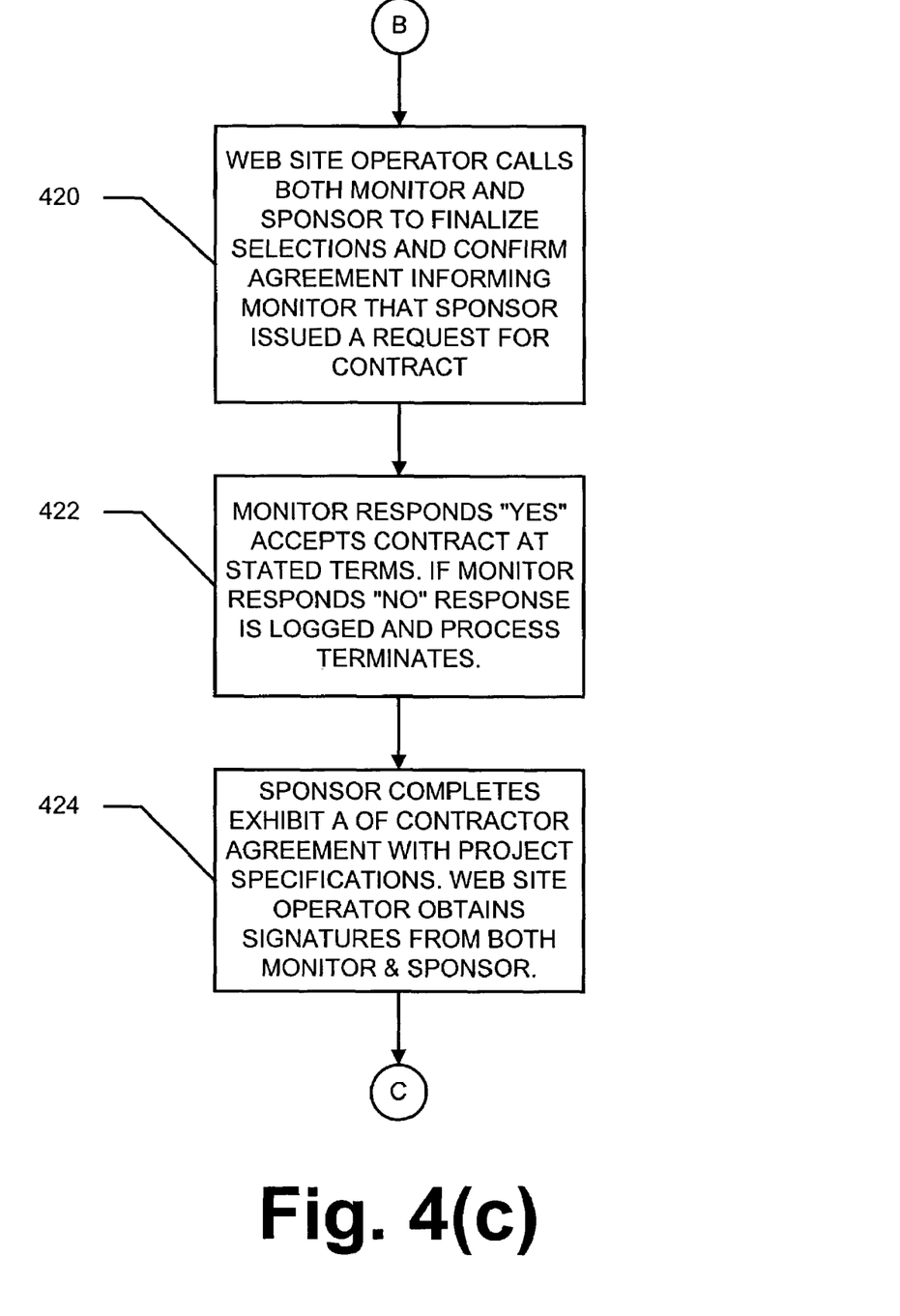

At step 420, an owner or operator of web site server entity 312 telephones the selected monitors and the sponsor to finalize the selections and confirm that the monitors still desire to work on the project and that the sponsor still desires the selected monitors. Furthermore, at step 420, web site server entity 312 informs (e.g., via email or telephone) the selected monitors that the sponsor has issued a request for contract of their services. At step 422, each selected monitor may accept or decline the contract with the sponsor. If the monitor declines the contact, the method terminates for that monitor. At step 424, the sponsor sets forth the project specifications that are added to a section (known as "Exhibit A") of a Contractor Agreement, and submits them to web site server entity 312. The Contractor Agreement may be a typical independent contractor/employer agreement that includes the project specifications therein. Preferably, both monitors and sponsors have agreed to a standard contract provided on server web site entity 312, which significantly reduces the amount of paperwork associated with contracting monitors. Also at step 424, the owner or operator of web site server entity 312 obtains the signatures of each monitor and the sponsor on the Contractor Agreement (which may be obtained up front upon registration with server web site entity 312). Alternatively, the Contractor Agreement may be supplied on web site server entity 312, and signed with digital signatures. Monitors, by submitting their registration, may agree with a digital signature to adopt the standard agreement provided on server web site entity 312. Sponsors, by registering with server web site entity 312, may agree with a digital signature to adopt the standard agreement as well.

Figure 4D:
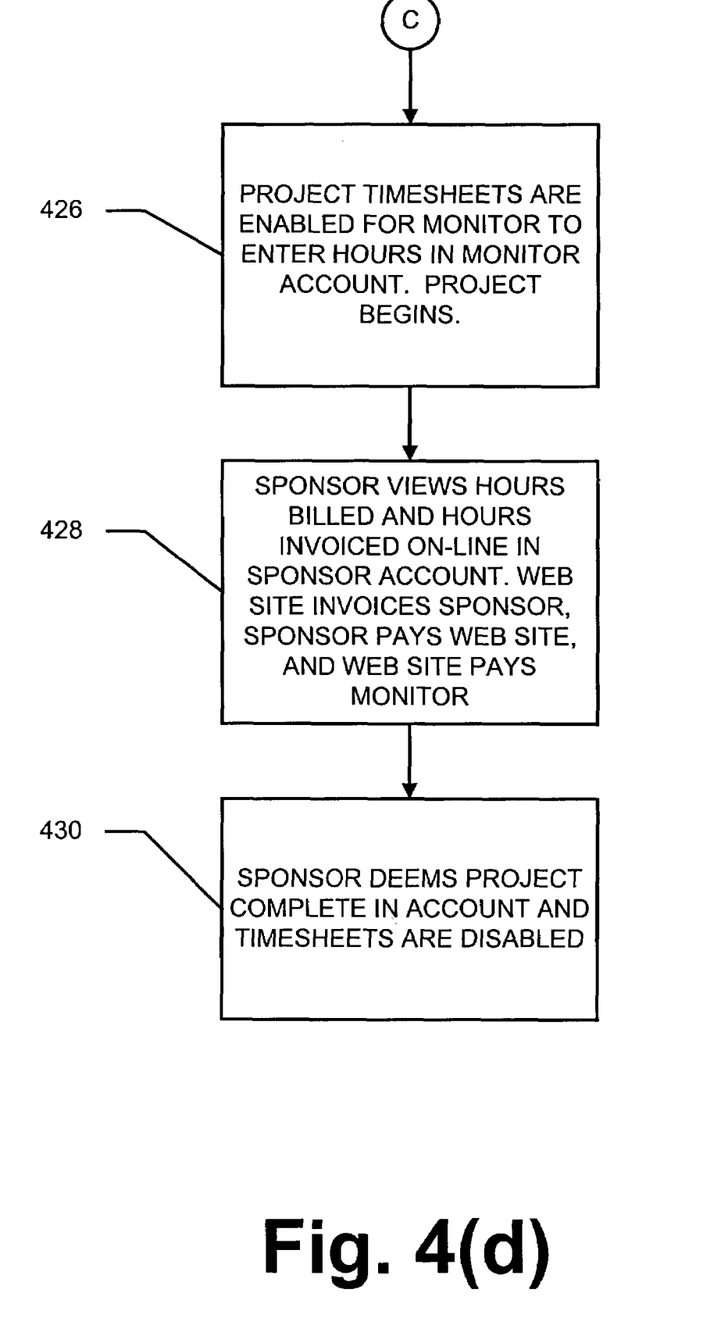

At step 426, web site server entity 312 enables project timesheets for the contracting monitors so that they may enter their hours for the project. The project also begins at step 426. At step 428, the web site server entity 312 uses the hours entered by the monitors to generate invoices that are sent to the sponsor of the project. The project sponsor may view the hours billed and the hours invoiced at web site server entity 312, via their account. Also at step 428, the web site server entity 312 automatically invoices the sponsor, the sponsor pays the invoice price electronically or by conventional means to the web site server entity 312 and an outside firm (e.g., an accounting firm) may then electronically directly deposit the amount due to the monitor into the monitor's bank account. Once the sponsor deems the project complete, as shown at step 430, web site server entity 312 will disable the project timesheets for the contracting monitors.

The system and method of the present invention provides unparalleled (24 hours per day, 365 days per year) access, and provides an efficient, confidential, and secure way to identify qualified and available independent clinical monitors. The system and method of the present invention dramatically reduces the time and cost of searching for qualified people needed to conduct studies. Furthermore, the present invention provides benefits to both sponsors and monitors. For example, through the system and method, sponsors may quickly build a professional team of independent monitors in hours versus weeks of conventional methods. By providing their credentials and availability, clinical monitors have more control over their schedule and careers, and receive higher compensation for their work.

It will be apparent to those skilled in the art that various modifications and variations can be made in the computer-implemented system and method of matching monitors and sponsors of the present invention and in construction of this system and method without departing from the scope or spirit of the invention. As an example, the system and method of the present invention could also allow the monitors to post their paper Curriculum Vitae ("CV") on server web site entity 312.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for matching clinical monitors with clinical sponsors, comprising:

receiving, by a computer, an agreement to enter into a standard contract from clinical monitors and a clinical sponsor;

creating a monitor profile for each of the clinical monitors, the monitor profiles including region information of the clinical monitors;

prescreening the monitor profiles to ensure they meet predetermined qualifications;

blinding, by the computer, the monitor profiles from the clinical sponsor;

maintaining, by the computer, a project management section for receiving project information;

receiving the project information for a project from the clinical sponsor into the project management section, the received project information identifying multiple study site locations for the project;

blocking, by the computer, the clinical monitors from viewing the project information received in the project management section;

performing a blinded search of the monitor profiles based upon predetermined search criteria, the search criteria including the region information of the clinical monitors;

generating, by the computer, a list of qualified clinical monitors from the blinded search of the monitor profiles;

selecting from the list of qualified clinical monitors a plurality of the qualified clinical monitors from at least two different regions to view the project information for the project in the project management section;

unblocking the selected clinical monitors from viewing the project information for the project in the project management section;

issuing invitations to the selected clinical monitors informing the selected clinical monitors that the selected clinical monitors have been selected to interview for the project;

receiving acceptance of the invitations from accepting selected clinical monitors;

unblinding, by the computer, the contact information of the accepting selected clinical monitors;

receiving requests from the clinical sponsor to enter into a project specific contract for the project with a plurality of the accepting selected clinical monitors subsequent to the interviews for the project;

receiving acceptance of the project specific contract for the project from a plurality of the requested clinical monitors;

adding information from the project specific contract to the standard contract for the accepting requested clinical monitors upon receipt of acceptance of the project specific contract by the accepting requested clinical monitors; and assigning, by the computer, the accepting requested clinical monitors to the project of the clinical sponsor after acceptance of the project specific contract for the project, at least two of the accepting requested clinical monitors from different regions;

wherein the computer is a third party system.

2. A computer-implemented method for matching clinical monitors with clinical sponsors as recited in claim 1, wherein the monitor profile creation step comprises inputting a calendar of availability.

3. A computer-implemented method for matching clinical monitors with clinical sponsors as recited in claim 1, further comprising: storing the monitor profiles.

4. A computer-implemented method for matching clinical monitors with clinical sponsors as recited in claim 1, wherein the inputting project information step comprises inputting start and end dates, percent of time commitment, estimated days on site, and the multiple study site locations for the project.

5. A computer-implemented method for matching clinical monitors with clinical sponsors as recited in claim 4, further comprising: storing the project information.

6. A computer implemented method for matching clinical monitors with clinical sponsors as recited in claim 1, further comprising:
enabling communication among the two or more monitors and the sponsor for collaboration on the project.

7. A computer implemented method for matching clinical monitors with clinical sponsors as recited in claim 1, further comprising:
receiving timesheet information for the project from the two or more monitors; and
generating payment invoices for the two or more monitors based on the received time sheets.

8. The computer-implemented method of claim 1, wherein the unblocking step comprises:
allowing the accepting selected clinical monitors to screen the project information in the project management section prior to receiving acceptance of the project specific contract for the project from the plurality of the requested clinical monitors.

9. A system for matching clinical monitors with clinical sponsors, the system comprising:
a memory configured to store instructions; and
a processor configured to execute instructions for:
receiving an agreement to enter into a standard contract from clinical monitors and a clinical sponsor;
creating a monitor profile for each of the clinical monitors, the monitor profiles including region information of the clinical monitors,
prescreening the monitor profiles to ensure they meet predetermined qualifications,
blinding the monitor profiles from the clinical sponsor,
maintaining a project management section for receiving project information,
receiving the project information for a project from the clinical sponsor into the project management section, the received project information identifying multiple study site locations for the project,
blocking the clinical monitors from viewing the project information receiving in the project management section,
enabling a blinded search of the monitor profiles for the qualified clinical monitors based upon predetermined search criteria, the search criteria including the region information of the clinical monitors,
generating a list of qualified clinical monitors from the blinded search of the monitor profiles,
enabling selection of a plurality of the qualified clinical monitors from at least two different regions to view the project information for the project in the project management section,
receiving the selection of the plurality of qualified clinical monitors to view the project information for the project in the project management section;
unblocking the selected clinical monitors from viewing the project information for the project in the project management section,
issuing invitations to the selected clinical monitors informing the selected clinical monitors that the selected clinical monitors have been selected to interview for the project,
receiving acceptance of the invitations from accepting selected clinical monitors,
unblinding the contact information of the accepting selected clinical monitors,
receiving requests from the clinical sponsor to enter into a project specific contract for the project with a plurality of the accepting selected clinical monitors subsequent to the interviews for the project,
receiving acceptance of the project specific contract for the project from a plurality of the requested clinical monitors,
adding information from the project specific contract to the standard contract for the accepting requested clinical monitors upon receipt of acceptance of the project specific contract by the accepting requested clinical monitors, and
assigning the accepting requested clinical monitors to the project of the clinical sponsor after acceptance of the project specific contract for the project, at least two of the accepting requested clinical monitors from different regions.

10. A system for matching clinical monitors with clinical sponsors as recited in claim 9, wherein the monitor profile creation instruction comprises inputting a calendar of availability.

11. A system for matching clinical monitors with clinical sponsors as recited in claim 9, wherein the processor is further configured to execute instructions for storing the monitor profiles.

12. A system for matching clinical monitors with clinical sponsors as recited in claim 9, wherein the inputting start and end dates, percent of time commitment, estimated days on site, and study site locations for the project.

13. A system for matching clinical monitors with clinical sponsors as recited in claim 12, wherein the processor is further configured to execute instructions for storing the project information.

14. A system for matching clinical monitors with clinical sponsors as recited in claim 9, the processor further configured to execute instructions for:
   enabling communication among the monitors and the sponsor for collaboration on the project.

15. A system for matching clinical monitors with clinical sponsors as recited in claim 9, the processor further configured to execute instructions for:
   receiving timesheet information for the project from the monitors; and
   generating payment invoices for the monitors based on the received time sheets.

16. A computer-implemented method for matching clinical monitors with clinical sponsors, comprising:
   providing a web site that includes a searchable database of clinical monitor profiles, the monitor profiles blinded from the clinical sponsors by a computer, the monitor profiles including region information of the clinical monitors, and a project management section for receiving project information within the computer for a project inputted by a clinical sponsor, the project information identifying multiple study site locations for the project;
   blocking, by the computer, the clinical monitors from viewing the project information received in the project management section;
   receiving an agreement to enter into a standard contract from each clinical monitor and the clinical sponsor;
   providing a search criteria input system which implements a search input process, the search criteria input system providing the clinical sponsor with various search criteria from which the clinical sponsor may choose to vary the scope of a blinded search of the monitor profiles for qualified clinical monitors, the search criteria including the region information of the clinical monitors;
   displaying the qualified clinical monitors who meet the search criteria;
   selecting from the qualified clinical monitors who meet the search criteria a plurality of the qualified clinical monitors from at least two different regions to view the project information for the project in the project management section;
   unblocking, by the computer, the selected clinical monitors from viewing the project information for the project in the project management section;
   issuing invitations to the selected clinical monitors informing the selected clinical monitors that the selected clinical monitors have been selected to interview for the project;
   receiving acceptance of the invitations from accepting selected clinical monitors,
   unblinding, by the computer, the contact information for each of the accepting selected clinical monitors, the contact information being stored in the searchable database of clinical monitor profiles;
   receiving requests from the clinical sponsor to enter into a project specific contract for the project with a plurality of the selected clinical monitors;
   receiving acceptance of the project specific contract for the project from a plurality of the requested clinical monitors;
   adding information from the project specific contract to the standard contract for the accepting clinical monitors upon receipt of acceptance of the project specific contract by the accepting clinical monitors; and
   assigning the accepting clinical monitors to the project of the clinical sponsor after acceptance of the project specific contract for the project, at least two of the accepting clinical monitors from different regions;
   wherein the computer is a third party system.

17. A computer-implemented method for matching clinical monitors with clinical sponsors as recited in claim 16, wherein the project information includes start and end dates, percent of time commitment, estimated days on site, and study site locations for the project.

18. A computer-implemented method for matching clinical monitors with clinical sponsors as recited in claim 16, wherein the clinical monitor profiles include a calendar of availability.

19. A computer-implemented method for matching clinical monitors with clinical sponsors as recited in claim 16, wherein, prior to the displaying step, the method further comprises comparing the search criteria to the information stored in the searchable database of clinical monitor profiles.

20. A computer-implemented method for matching clinical monitors with clinical sponsors as recited in claim 16, further comprising:
   enabling communication among the monitors and the sponsor for collaboration on the project.

21. A computer-implemented method for matching clinical monitors with clinical sponsors as recited in claim 16, further comprising:
   receiving timesheet information for the project from the monitors; and
   generating payment invoices for the monitors based on the received time sheets.

22. A system for matching clinical monitors with clinical sponsors, comprising:
   a memory configured to store instructions; and
   a processor configured to execute instructions for:
   providing a web site that includes a searchable database of clinical monitor profiles, the monitor profiles blinded from the clinical sponsors, the monitor profiles including region information of the clinical monitors and a project management section for receiving project information for a project inputted by a clinical sponsor, the project information identifying multiple study site locations for the project,
   blocking the clinical monitors from viewing the project information received in the project management section,
   receiving an agreement to enter into a standard contract from each clinical monitor and the clinical sponsor,
   providing a search criteria input system which implements a search input process, the search criteria input system providing the clinical sponsor with various search criteria from which the clinical sponsor may choose to vary the scope of a blinded search of the monitor profiles for qualified clinical monitors, the search criteria including the region information of the clinical monitors, displaying the qualified clinical monitors who meet the search criteria, and enabling selection of a plurality of the qualified clinical monitors from at least two different regions to view the project information for the project in the project management section, receiving the selection of the plurality of the qualified clinical monitors to view the project information for the project in the project management section;

unblocking the selected clinical monitors from viewing the project information for the project in the project management section, issuing invitations to the selected clinical monitors information the selected clinical monitors that the selected clinical monitors have been selected to interview for the project, receiving acceptance of the invitations from accepting selected clinical monitors, unblinding the contact information for each of the accepting selected clinical monitors, the contact information being stored in the searchable database of clinical monitor profiles, receiving requests from the clinical sponsor to enter into a project specific contract for the project with a plurality of the selected clinical monitors, receiving acceptance of the project specific contract for the project from a plurality of the requested clinical monitors, adding information from the project specific contract to the standard contract for the accepting clinical monitors upon receipt of acceptance of the project specific contract by the accepting clinical monitors; and assigning the accepting clinical monitors to the project of the clinical sponsor after acceptance of the project specific contract for the project, at least two of the accepting clinical monitors from different regions.

23. A system for matching clinical monitors with clinical sponsors as recited in claim 22, wherein the project information includes start and end dates, percent of time commitment, estimated days on site, and study site locations for the project.

24. A system for matching clinical monitors with clinical sponsors as recited in claim 22, wherein the clinical monitor profiles include a calendar of availability.

25. A system for matching clinical monitors with clinical sponsors as recited in claim 22, wherein prior to the displaying instruction, the processor is further configured to execute instructions for comparing the search criteria to the information stored in the searchable database of clinical monitor profiles.

26. A system for matching clinical monitors with clinical sponsors as recited in claim 22, the processor further configured to execute instructions for:

enabling communication among the monitors and the sponsor for collaboration on the project.

27. A system for matching clinical monitors with clinical sponsors as recited in claim 22, the processor further configured to execute instructions for:

receiving timesheet information for the project from the monitors; and generating payment invoices for the monitors based on the received time sheets.

28. A computer-implemented method for matching clinical monitors with clinical sponsors, comprising:

creating, by a computer, a monitor profile for each of the clinical monitors;

prescreening the monitor profiles to ensure they meet predetermined qualifications;

blinding, by the computer, the monitor profiles from the clinical sponsors;

maintaining, with the computer, a project management section for receiving project information;

receiving the project information for a project from the clinical sponsor into the project management section;

blocking, by the computer, the clinical monitors from viewing project information received in the project management section;

performing a blinded search of the monitor profiles based upon predetermined search criteria;

generating, by the computer, a list of qualified clinical monitors from the blinded search of the monitor profiles;

selecting from the list of qualified clinical monitors a plurality of the qualified clinical monitors to view the project information for the project in the project management section;

unblocking, by the computer, the selected clinical monitors from viewing the project information for the project in the project management section;

issuing invitations to the selected clinical monitors informing the selected clinical monitors that the selected clinical monitors have been selected to interview for the project;

receiving acceptance of the invitations from accepting selected clinical monitors; and unblinding, by the computer, the contact information of the accepting selected clinical monitors;

wherein the computer is a third party system.

* * * * *

UNITED STATES PATENT AND TRADEMARK OFFICE
CERTIFICATE OF CORRECTION

| | | |
|---|---|---|
| PATENT NO. | : 7,647,240 B2 | Page 1 of 1 |
| APPLICATION NO. | : 10/298316 | |
| DATED | : January 12, 2010 | |
| INVENTOR(S) | : Freedman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1623 days.

Signed and Sealed this

Sixteenth Day of November, 2010

David J. Kappos
*Director of the United States Patent and Trademark Office*